(12) United States Patent
Abrams et al.

(10) Patent No.: US 6,194,609 B1
(45) Date of Patent: *Feb. 27, 2001

(54) CRYSTALLIZATION IN A PLATE HEAT EXCHANGER

(75) Inventors: Kenneth J. Abrams; Thomas M. Bartos; Debra J. Streich, all of Naperville, IL (US)

(73) Assignee: BP Amoco Corporation, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/021,585

(22) Filed: Feb. 10, 1998

Related U.S. Application Data

(60) Provisional application No. 60/051,198, filed on Jun. 30, 1997.

(51) Int. Cl.⁷ .................................................. C07C 51/42
(52) U.S. Cl. ............................................ 562/486; 585/812
(58) Field of Search ............................ 562/486; 585/812, 585/815, 813

(56) References Cited

U.S. PATENT DOCUMENTS

| | | |
|---|---|---|
| 3,497,552 | 2/1970 | Olsen .................................... 260/525 |
| 3,584,039 | 6/1971 | Meyer .................................... 260/525 |
| 3,726,915 | 4/1973 | Pohlmann ............................. 260/525 |
| 4,162,617 | 7/1979 | Schmidt et al. ........................ 62/123 |
| 4,214,072 * | 7/1980 | Sterzel et al. ......................... 528/272 |
| 4,235,844 * | 11/1980 | Sterzel et al. ......................... 422/138 |
| 4,405,809 | 9/1983 | Stech et al. ............................ 562/487 |
| 4,452,302 | 6/1984 | Schoerner ............................. 165/133 |
| 4,981,190 | 1/1991 | Nakayama et al. ................... 180/197 |
| 5,333,681 | 8/1994 | Jullien et al. ............................ 165/82 |
| 5,510,499 * | 4/1996 | Mendoza-Frohn et al. .......... 549/229 |
| 5,523,064 | 6/1996 | Schrantz ............................. 422/245.1 |
| 5,584,341 | 12/1996 | Sabin et al. ........................... 165/166 |
| 5,626,051 | 5/1997 | Sabin ................................... 72/379.6 |
| 5,630,475 | 5/1997 | Sabin et al. ........................... 165/281 |

FOREIGN PATENT DOCUMENTS

| | | | |
|---|---|---|---|
| 19627847 | 1/1998 | (DE) .............................. C07C/57/07 |
| 9324440 | 12/1993 | (WO) ............................. C07C/63/26 |

* cited by examiner

Primary Examiner—Samuel Barts
(74) Attorney, Agent, or Firm—Phyllis Turner-Brim; Stephen L. Hensley

(57) ABSTRACT

Crystallization of a crystallizable material is achieved through heat exchange in a plate heat exchanger is disclosed. A mixture or solution comprising a crystallizable material is passed through a plate heat exchanger at an appropriate temperature and pressure such that the material is selectively crystallized. The processes are particularly useful in the production of para-xylene, dimethylnaphthalene, aromatic carboxylic acids, and aromatic anhydrides.

13 Claims, 1 Drawing Sheet

CRYSTALLIZATION IN A PLATE HEAT EXCHANGER

CROSS-REFERENCE TO RELATED APPLICATIONS

This application claims priority of U.S. Provisional Application No. 60/051,198, filed Jun. 30, 1997, and U.S. patent application Ser. No. 08/961,102 filed Oct. 30, 1997 which are both incorporated in their entirety herein by reference.

FIELD OF THE INVENTION

This invention relates to the use of plate heat exchangers to selectively crystallize a crystallizable material present in a fluid mixture or solution. More specifically, this invention relates to selectively crystallize a material present in a fluid mixture or solution by heat exchange in plate heat exchangers.

BACKGROUND OF THE INVENTION

Separations of a particulate solid or crystalline phase from a liquid phase by cooling, evaporation, or both are well known. For example, separation of salt from sea water by solar-evaporation may be prehistoric.

Crystallization is important in the preparation of a pure product, since a crystal usually separates out as a substance of definite composition, from a solution or mixture of varying composition. Impurities in the mother liquor are carried into the crystalline product only to the extent that they adhere to the surface or are occluded within the crystals which may have grown together during crystallization.

Crystallization by flash evaporation has also been used to obtain substantially instantaneous decrease in both temperature and pressure, and the attendant substantially instantaneous evaporation of solvent as the relatively hot solution is introduced into the flash crystallization vessel. The rapidly vaporized solvent flashed to the vapor phase permits rapid removal of solvent vapor. Both crystallization and crystal growth occur rapidly with the cooling and concentrating caused by flashing the solution to the lower temperature. Growth of crystals is, substantially, entirely at the lower temperature and is independent of residence time.

Heat exchangers of varying kinds are routinely used in commercial industrial operations. Heat exchangers are used to transfer heat energy from one fluid to another through a heat transfer medium which maintains the integrity of the each fluid stream. In conventional heat exchangers, two fluid streams that remain separate are directed such that heat is transferred from one stream to the other stream through a solid heat transfer medium. The amount of heat transferred between the two fluids depends upon many factors including: the configuration of the heat exchange flow paths, the surface area available to facilitate heat transfer, the heat transfer coefficient of the heat transfer medium, the temperature difference between the exchange fluids, the pressure drop between the inlet and outlet of each fluid stream, and many others.

One example of a typical heat exchanger is commonly called a shell-and-tube heat exchanger. In its simplest form, this type of heat exchanger consists of a small tube disposed within a tube of larger diameter. In the shell-and-tube exchanger, one fluid flows through the smaller inner tube, while the other flows in the annulus created between the outside surface of the smaller tube and the inside surface of the larger tube. Heat is transferred between the two fluids through the smaller inner tube. Accordingly, one fluid increases in energy, while the other decreases in energy. The fluid stream that increases in energy is generically referred to as the "hot side" of the heat exchanger, while the fluid stream that decreases in energy is generically referred to as the "cold side" of the heat exchanger.

Heat exchange between the fluids does not necessary translate into an increase or decrease in the temperature for either fluid stream. Heat exchangers are often used simply to effect a phase change in one of the fluid streams. For example, a heat exchanger may be used to transfer to or from a fluid stream an amount of heat necessary to gasify a liquid stream, or liquefy a gaseous stream, in which case the stream may leave the heat exchanger without a substantial change in temperature.

Traditionally, a major problem in carrying out industrial crystallization by heat exchange, for example in a conventional heat exchanger, is that the crystalline solids deposit on the surface through which heat is transferred, a phenomenon referred to here as fouling. Such fouling reduces the rate of heat transfer and make necessary frequent shutdowns for cleaning of equipment.

Designers of industrial crystallizes have attempted to abate fouling by providing scrapers to continuously remove solid deposits from the heat transfer surface. Such designs typically comprise a set of horizontal jacketed pipes each having a centrally located rotating shaft with peripheral scrapers. Solution of the material to be crystallized is pumped through the inner pipe while cooling fluid is concurrently pumped through the annulus. Heat is extracted from the solution, crystals are formed, and fouling develops on the wall of the inner pipe. Rotating scrapers remove, at least in part, solids from heat transfer surface.

Scrapers have proven to be somewhat effective by increasing run duration from a few minutes or hours to one to fourteen or more days. However, at commercially acceptable heat fluxes the scrapers and rotating shafts themselves become fouled. The solids can become so thick that the inner pipe becomes plugged or the rotating members are damaged. Before this happens it is necessary to shut down the crystallizer and clean the inner pipe, for example by heating it to melt the solid deposits, by washing it with solvent or by manually scraping it.

Other commercially available crystallizers include a set of internally cooled plates disposed in a vertical or horizontal tank. Such designs usually include a rotating shaft to which wipers are attached. Wipers are positioned so that the surfaces of the plates are wiped as the shaft rotates. However, if the temperature differential is increased to provide a good production rate, the shaft, wipers or plates rapidly become fouled requiring an interruption in operation to melt off the solids.

Attempts at improving conventional designs have further comprised heating the scrapers with electric or hot fluid tracers while the scrapers are rotating. Although this can be somewhat effective, doing so usually puts a great deal of heat back into the solution to be cooled and thus limits the capacity of the equipment in addition to increasing operating cost. In any event, the effective installation of heaters on mechanically complicated scrapers is difficult and expensive.

The rate of fouling generally increases rapidly as the difference in temperature between the solution and the cooling fluid increases. As a practical matter, operators of crystallizers generally limit the temperature differential to a magnitude at which they are able to get a fairly long run time between cleanings. However, operating at low temperature differentials requires relatively large surface areas and correspondingly large capital investment to provide commercially acceptable capacity. Accordingly, the ability to use higher temperature differentials would likely result in a substantial reduction in crystallizer capital cost.

British patent No. 1,365,536 discloses a counter-current crystallizer apparatus which comprises individual crystallization, purification, and melt sections. Each purification section comprises a plurality of perforated plates positioned at spaced intervals in a cylindrical enclosure so that the crystal mass may pass the plates counter-currently to the mother liquor. Free moving bodies, such as spheres, are placed on each perforated plate. The spheres are set in motion by vibrating the entire column, vibrating the set of perforated plates or by other means. Although this invention does increase the purification efficiency, it still suffers from the short run time characteristic of conventional crystallizers because this invention incorporates conventional chillers to generate the crystal crop that is subsequently purified in the above-described purification section, and crystallization in tubes tends to cause plugging.

U.S. Pat. No. 4,981,190 to Carter et al. describes a type of crystallizer having a plurality of vibrating perforated plates at intervals along the crystallizer length. More particularly the patent discloses a crystallizer column including a plurality of substantially horizontal perforated plates periodically attached to a central shaft located coaxially within a normally elongated housing. A plurality of heat transfer tubes extend along the axial length of the column through apertures fabricated in the horizontal plates. Mobile bodies substantially cover the surface area of each perforated plate. A material excitation device which is said to produce two waveforms is attached to the central shaft. Frequency waveform that results in the mobile bodies colliding with one another, the inner surface of the enclosure and the surface of the heat transfer tubes. The second waveform is a high amplitude, low frequency waveform that causes the plates to move along the length of the heat transfer surfaces so that the surfaces are scraped of any fouling that occurs.

U.S. Pat. No. 5,523,064 to Schranz describes a surface-cooled fluid bed crystallizer apparatus using submerged heat exchanger surfaces (typically heat exchanger tubes or plates through which a coolant is passed) which surfaces are bathed with a stream of gas bubbles (preferably air). Gas bubbles are said to increase localized velocity at the heat exchanger surfaces, improve heat transfer, reduce crystallization on the heat exchanger surfaces and gently keep crystals in suspension, thereby avoiding unwanted nucleation as is characterized by the use of mechanical circulation devices. Operation requires, however, continuous recalculation and the removal of depleted magma and crystals, in a continuous mode.

Laboratory evaluations indicate that heat transfer surfaces in crystallizers can be kept clean by inducing ultrasonic vibrations in them. This method does in fact work well in laboratory apparatus. Unfortunately, no way has been found to scale up ultrasonic crystallizer units to a commercially acceptable capacity.

Commonly assigned U.S. Pat. No. 3,497,552 to Olsen discloses that purification of impure organic materials dissolved in a liquid, such as water, can be accomplished by continuous crystallization in a plurality of series connected cooling stages. The cooling stages are facilitated by the addition of cooled solvent at each stage. Unfortunately, this requires extensive solvent handling which is generally undesirable.

An additional barrier to the use of heat exchangers for crystallization, has been the tendency of the crystalls to accumlate within the heat exchanger and thereby plug the heat exchanger flow. This could result in a dangerous situation because of pressure build-up caused by the plugging which might lead to a violent rupture.

It is therefore a general object of the present invention to provide an improved process for phase separating, from a solution or mixture, a material present therein by crystallizing it through heat exchange which overcomes the aforesaid problems of prior art methods.

It is another object of the present invention to provide a method for selectively crystallizing, from a fluid mixture or solution a material present therein, the chemical material by continuous heat exchange in a plate heat exchanger thereby forming a slurry comprising crystals of the chemical material and a resulting mother liquor.

It is yet another object of the present invention to provide a method of crystallization of para-xylene, dimethylnaphthalene and aromatic carboxylic acids and anhydrides which reduces the necessary equipment and reduces overall solvent handling compared to prior art processes.

Other objects and advantages of the invention will become apparent upon reading the following detailed description and appended claims.

SUMMARY OF THE INVENTION

According to the current invention, a material present in a fluid mixture or solution is selectively crystallized through heat exchange in a plate heat exchanger. The methods of the current invention can be used to yield a relatively pure material from an impure fluid mixture or solution. According to the current invention, a material present in fluid mixture or solution can be selectively crystallized in a plate heat exchanger through heat exchange whereby the mixture or solution is brought to an appropriate temperature and pressure such that the material is phase separated in relatively pure form by crystallization. In this regard, the current invention is useful when the impurities that contaminate the material remain soluble in the solvent at the pressure and temperature at which the relatively pure material is crystallized.

In one embodiment, the material that is crystallized comprises a hydrocarbon material. In another embodiment, the material that is crystallized comprises an organic material. In still another embodiment, the material that is crystallized comprises an aromatic organic material. In yet another embodiment, the material comprises para-xylene, dimethylnaphthalene, or aromatic carboxylic acids or anhydrides. In a further embodiment, the material is selected from the group consisting of para-xylene, dimethylnaphthalene, terephthalic acid ("TA"), purified terephthalic acid ("PTA"), isophthalic acid ("IPA"), purified isophthalic acid ("PIA"), trimellitic acid, trimellitic anhydride, naphthalenedicarboxylic acid ("NDA"), tertiery-butyl isophthalic acid ("TBIA"), biphenyldicarboxylic acid, pyromellitic acid, pyromellitic anhydride and oxybisbenzoic acid.

One embodiment of the present invention provides for an integrated process in which crystallization and purification operations are combined, and which is particularly useful when the material to be crystallized comprises an aromatic material produced, for example, by the liquid phase oxidation of a corresponding suitable aromatic compound. This embodiment includes:

(a.) heating a slurry comprising solid particulates of impure aromatic material and a solvent on the hot side of a plate heat exchanger until the particulates are substantially dissolved in the solvent thereby forming a first solution;

(b.) passing the first solution through a bed of purification catalyst whereby the impure aromatic material is catalytically purified resulting in a second solution of relatively pure aromatic material;

(c.) cooling the second solution of relatively pure aromatic carboxylic acid on the cold side of the plate heat exchanger to selectively crystallize the relatively pure aromatic carboxylic acid thereby forming a slurry of crystals of relatively pure aromatic carboxylic acid and a resultant mother liquor.

Importantly, the methods of the current invention avoid solvent flashing and flash cooling. In addition, flashing across valves and other pressure reducers or controlling devices to cause plugging by substantially instantaneous solid formation is substantially eliminated. Also, overall solvent handling is generally reduced.

An important aspect of the current invention is that combines crystallization and heat exchange operations. In many commercial operations, one apparatus is used for crystallization, while a second apparatus is used for heat exchange. By combining these two operations within a single apparatus, a significant capital cost savings may be realized.

In one aspect the invention is a process for purification of a relatively impure material soluble in a fluid solvent, and having as impurity one or more materials which remain soluble at the temperatures and pressures at which the relatively pure material is crystallized. Preferably the impurities are 5 to 10 times more soluble than the soluble material at the same temperatures and pressures. Preferably content of such impurity does not exceed at least one impurity solubility in the fluid solvent at the temperatures and pressures of crystallization.

Purification of such material according to the invention comprises:

(a.) dissolving in a fluid solvent the relatively impure material at appropriate temperature and pressure to obtain a first solution of the relatively impure material substantially at its saturation concentration;

(b.) passing the first solution through a particulate bed of purification catalyst to generate a second solution of relatively pure material;

(c.) bringing the second solution to an appropriate temperature for crystallization of the material by heat exchange in a plate heat exchanger to effect phase separation of the relatively pure material from a resultant mother liquor by crystallization; and (d.) recovering from the mother liquor crystals of the relatively pure material.

Still another embodiment of the current invention is a process for purification and crystallization of a aromatic carboxylic acid in a suitable solvent. The process generally comprises:

(a.) passing a solution of from about 5 to about 50 weight percent of the impure aromatic carboxylic acid at conditions of temperature and pressure sufficient to maintain the solution substantially in the liquid phase, through a particulate bed of purification catalyst and in the presence of a molecular hydrogen-containing gas;

(b) cooling the solution in a plate heat exchanger to thereby effect phase separation of relatively pure aromatic carboxylic acid from a resultant mother liquor by crystallization; and (c) recovering purified aromatic carboxylic acid product from the resulting mother liquor while maintaining temperatures within a range downward from about 150° C. to about 25° C.

In yet another aspect, processes of this invention comprise:

(a.) heating a slurry comprising particulates of the impure aromatic carboxylic acid in an aqueous medium in a plate heat exchanger to obtain a first solution;

(b) passing the first solution of impure aromatic carboxylic acid with organic impurities consisting of oxygen-containing aromatic co-products of oxidation and/or other organic components, through a particulate bed of purification catalyst comprising at least one noble metal supported under conditions suitable for decarbonylation and/or hydrogenation of organic impurities capable thereby forming a second solution; and (c.) cooling the second solution in a plate heat exchanger to effect crystallization of relatively pure aromatic carboxylic acid in the second solution; and (d.) physically separating the crystals of relatively pure aromatic carboxylic acid a resultant mother liquor.

In another aspect, processes of this invention the cooling of the solution of relatively pure aromatic carboxylic acid, which is preferably an aqueous solution, and the heating of the slurry of relatively impure solid particulates of aromatic carboxylic acid are carried out by passing, simultaneously and countercurrently, the slurry and the solution though a plate heat exchanger thereby transferring heat therebetween.

A preferred aspect of the present invention is a process for purification of a relatively impure aromatic dicarboxylic acid produced by catalytic liquid-phase oxidation, which purification comprises:

(a) heating a slurry of the solid particulates of impure aromatic dicarboxylic acid in an aqueous medium in a plate heat exchanger to thereby obtain a first aqueous solution of from about 5 to about 50 weight percent of the impure aromatic dicarboxylic acid at a temperature of from about 100° C. to about 350° C. and at a pressure above the pressure sufficient to maintain the solution substantially in the liquid phase;

(b) passing the first aqueous solution through a particulate bed of purification catalyst in the presence of a molecular hydrogen-containing gas whereby the impure acid is catalytically purified to form a second aqueous solution; and (c) cooling the second aqueous solution in a plate heat exchanger to effect separation of relatively pure aromatic dicarboxylic acid from the second aqueous solution by crystallization.

Preferably, the purification catalyst comprises a noble metal of Group VIII of the Periodic Table of Elements on a support which does not disintegrate in less than one month under the aforesaid conditions employed in the purification.

In general, plate heat exchangers useful in the current invention will be designed to withstand the pressure, temperature and flow requirements necessary as detailed below, and will further be designed to substantially reduce fouling and/or plugging over systems of the prior art.

In particular, plate heat exchangers useful the processes of this invention are, preferably, of the type having a plate bundle disposed within a pressure vessel and comprising a stack of mutually parallel metal heat-exchange plates. Each of the heat exchange plates includes smooth-surfaced edges and a corrugated central part to form, with associated heat-exchange plates, a double circuit for circulation of two independent fluids in counterflow. Additionally, the heat-exchange plates have longitudinal edges connected to one another by a connection means, and comprise a zone of heat transfer and exchange between the fluids. Further, the free ends of the heat-exchange plates have a zone for inlet and a zone for outlet of each of the fluids. The fluid inlet and outlet zones are formed by plane ends of the heat-exchange plates, between which independent plates provided with reliefs for distributing the fluids in a heat-exchange zone are inserted. Each independent plate is provided with reliefs including at least one zone for guiding one of the fluids to the corresponding circuit and a zone, for weak circulation of the fluid, separated from the guide zone by at least one transition zone allowing the fluid to pass between the guide zone and the circulation zone.

Guide zones of the plate bundle used in the invention preferably include continuous corrugations. These continuous corrugations of the guide zone form, preferably with the plane ends of the heat-exchange plates, fluid-circulation channels of constant cross-section and directed towards the corresponding circuits. Circulation zones of the plate bundle used in the invention include pins for maintaining separation from the plane ends of associated heat-exchange plates.

Transition zones of the plate bundle used in the invention include, preferably, longitudinally discontinuous corrugations forming passages between the guide zone and the weak-circulation zone.

Independent plates of the plate bundle used in the invention are, preferably, provided with reliefs including, at their longitudinal edges, blocks for fixing on and separation from the plane ends of the heat-exchange plates.

DETAILED DESCRIPTION OF THE INVENTION

Figure 1:
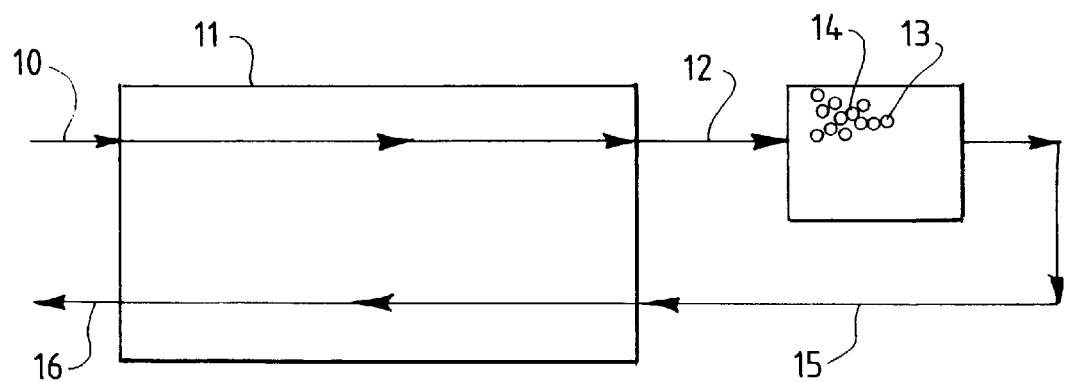
FIG. 1 is a schematic diagram of the process of one embodiment of the present invention.

A solution is, generally, any mixture of at least two components in a single phase. For purposes of the present invention "solution" is defined as a single liquid phase. Solubility of a given material is dependent upon a number of factors including temperature and the nature of the solvent. As a general rule the solubility of a solid in a liquid increases with increasing temperatures, but not in all systems (e.g., calcium hydroxide). The effect of pressure upon the solubility of a liquid in a liquid or a solid in a liquid is generally very small. No satisfactory method for estimating the extent to which a solid will dissolve in a given liquid has been developed.

Solubility data have been published for many systems, particularly for simpler two components systems. However, direct experimental determination of solubilities has been found advantageous for more complex multi-component systems such as are typically involved in purification processes according to this invention.

For example, quantity of water needed to dissolve terephthalic acid at various temperatures may be estimated from the table below:

| Terephthalic acid g/100 g of water | Temperature for solution, ° C. |
| --- | --- |
| 1 | 185 |
| 5 | 225 |
| 10 | 242 |
| 20 | 259 |
| 30 | 272 |

Processes of this invention may be applied to materials having water solubility of one percent by weight or less at 100° C. and increasing in solubility with temperature to within the range of 5 to 50 weight parts per 100 parts of water at 300° C. Crude organic chemical materials having this characteristic are referred to herein as being "sparingly soluble. The crude organic chemical materials further have impurities, preferably having solubilities in water at 100° C. from about 5 to about 10 times, and even from about 5 to about 100 times greater than the organic material to be purified in amounts not exceeding their saturation concentration in water at about 90° C. to about 110° C.

Preferably, processes of this invention operate on an aqueous solution at temperatures in a range from about 200° C. to about 350° C. and at pressures to maintain a liquid phase of water containing all of the sparingly soluble organic material to be purified in solution at that temperature range, preferably at a concentration such that the water is saturated at a temperature lower than the solution temperature, preferably about 10° C. lower, more preferably about 5° C. lower, most preferably about 2–3° lower, and free from materials not soluble in water at 200° C. to 350° C.

The crystallization processes of this invention are applicable, in general, to the recovery of organic materials soluble in an appropriate fluid solvent, where impurities have greater solubilities in the solvent at the desired temperatures and pressures, desirably 5 to 10 and even up to 100 times greater, than the material to be crystallized. Preferably, the impurities are present in an amount less than that required to exceed saturation of the solvent at the desired temperatures and pressures.

FIG. 1 is schematic illustration of one embodiment of the present invention in which the purification and crystallization processes are integerated. A first stream 10, comprising an aqueous slurry of impure aromatic dicarboxylic acid typically produced by catalytic liquid-phase oxidation, flows through one side of a plate heat exchanger 11. As the first stream is heated through heat exchange, the impure aromatic dicarboxylic acid is dissolved to form an aqueous solution of from about 5 to about 50 weight percent of impure aromatic dicarboxylic acid at a temperature of from about 100° C. to about 350° C., and at a pressure above the pressure sufficient to maintain the solution in substantially the liquid phase. For example, the solution might be maintained at a pressure that is 5.5 kg/cm2 above the pressure sufficient to maintain the solution in substantially the liquid phase.

A second stream 12 leaves the plate heat exchanger 11 and passed to a catalytic purification unit 13 which contains a particulate bed of purification catalyst 14. Optionally, a heater (not shown in FIG. 1) is disposed to heat the second stream 12 as it passes from the plate heat exchanger 11 to the catalytic purification unit 13. In he catalytic purification unit 13, at least a portion of the second stream 12 contacts the particulate bed of purification catalyst whereby the impure dicarboxylic acid is purified by hydrogenation. The purification catalyst preferably comprises a noble metal of Group VIII of the Periodic Table of Elements on a support that does not disintegrate in less than one month under the aforesaid conditions employed in the purification and in the presence of a hydrogen-containing gas.

A third stream 15 comprising an aqueous solution of relatively pure dicarboxylic acid flows from the catalytic purification unit 13 to the other side of the plate heat exchanger 11. In the plate heat exchanger, the third stream 15 is cooled by heat exchange with the first stream 10 whereby the relatively pure dicarboxylic acid is phase separated from the aqueous solution by crystallization. Accordingly, fourth steam 16 is a slurry comprising dicarboxylic acid crystals and a resulting mother liquor.

Heat exchangers suitable for processes in accordance with the present invention are a limited class of heat exchangers known a plate heat exchangers, which typically include a bundle of plates arranged side-by-side and mutually parallel. Suitable plate heat exchangers are those that are capable of functioning within the process parameters, and that have flow characteristics that allow for continuous operation without excessive fouling or plugging due to crystal formation. Preferably, the plate heat exchanger is capable of operating in a pressurized environment, for example, by being placed in a pressurized vessel. The disposition of the heat exchanger in a pressurized vessel facilitates operation of the heat exchanger at increased pressures, which are often dictated by the process.

Figure 2:
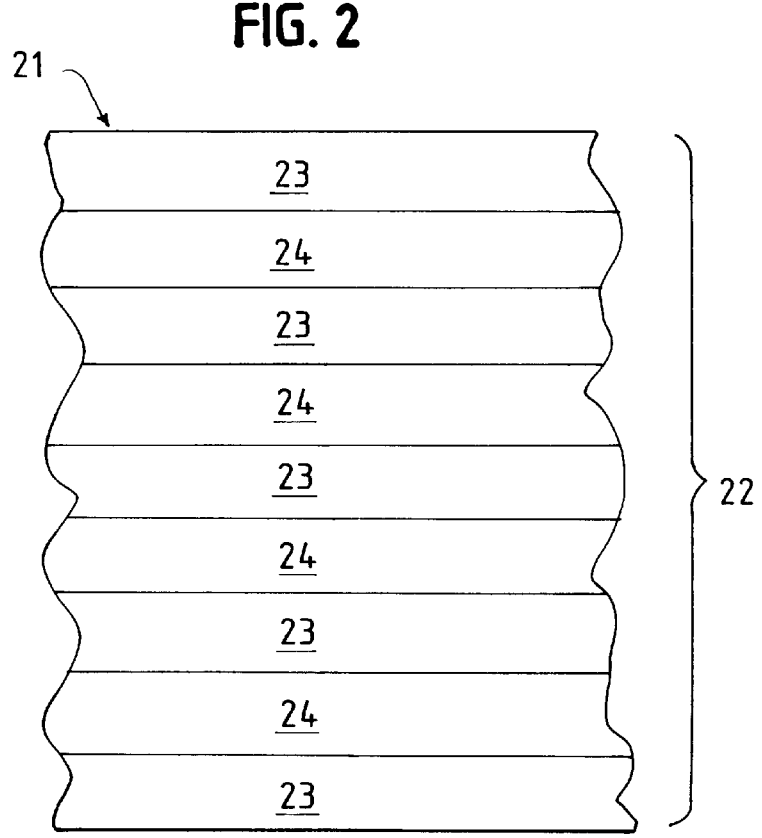
FIG. 2 is a cross-sectional illustration of a portion of a typical plate heat exchanger.

Turning now to FIG. 2, there illustrated is a cross-sectional view of a portion of a typical plate heat exchanger. Plate heat exchanger 21 comprises a plurality of substantially parallel plates 22. The plurality of plates 22 form a first circuit 23 and a second circuit 24. The fluids between which heat exchange is desired may flow concurrently or counter-currently through the first circuit 23 and the second circuit 24. Manifolds, headers, valves, pumps etc. (not shown in FIG. 2) are provided to direct each fluid to, through and from the plate heat exchanger 21 while maintaining the integrity of each fluid stream. If the plate heat exchanger is free-standing then the plurality of plates are typically disposed within a fluid tight casing.

Preferably, in the current invention, the plate heat exchanger is disposed within a pressurized vessel, for example as taught in U.S. Pat. No. 5,630,475 to Sabin et al. which is incorporated herein in its entirety by reference. Disposing the plate heat exchanger in a pressurized vessel allows operation at pressures substantially higher than ambient, e.g. greater than 400 psig.

Suitable plate heat exchangers are of the type taught in, for example, U.S. Pat. No. 5,584,341 to Sabin et al., and U.S. Pat. No. 5,626,051 to Sabin which are incorporated in their entirety herein by reference. In these heat exchangers, the plates, consisting of thin metal sheets, for example made of stainless steel, include smooth-surfaced edges and a central part provided with corrugations via which they are in contact with one another and by which they delimit a double circuit for circulation of two independent fluids in counterflow from one end of the exchanger to the other. The plates are connected to one another at their longitudinal edges by connection means consisting, for example, of longitudinal braces fixed together by a leak-tight weld wall extending over the entire length and over the entire height of the bundle.

In addition, the plates define a central zone for heat transfer and exchange between the fluids and, at each end of the bundle, a superposition of inlets and outlets for these fluids. In suitable structures, each plate includes particular corrugations distributed in defined directions on the surface of the plate, which define the central heat transfer and exchange zone as well as the inlets and the outlets. The inlets and the outlets are therefore formed by a superposition of corrugations which intersect, creating variations in passage cross-section for the fluids and thereby generating perturbations in their flow.

Heating and/or cooling of solutions of aromatic dicarboxylic acid produced by liquid-phase oxidation are carried out in plate heat exchangers of the type having a plate bundle disposed within a pressure vessel and comprising a stack of mutually parallel metal heat-exchange plates, each including smooth-surfaced edges and a corrugated central part to form, with the associated heat-exchange plates, a double circuit for circulation of two independent fluids in counterflow. The plates are connected to one another at their longitudinal edges by connection means and define, a zone of heat transfer and exchange between the fluids and, at their free ends, a zone for inlets and outlets of the fluids. The fluid inlet and outlet zones are formed by the ends of the heat-exchange plates, between which independent plates provided with reliefs for distributing the fluids in the heat-exchange zone are inserted.

According to other characteristics of the suitable plate heat exchangers taught in the above-referenced U.S. patents:

(a.) the set of plane plates and of plates provided with reliefs define, at each end of the bundle, a superposition with at least one inlet for one of the fluids and at least one outlet for the other of the said fluids;

(b.) each plate provided with reliefs includes at least one zone for guiding one of the fluids to the corresponding circuit and a zone, for weak circulation of this fluid, separated from the fluid zone by at least one transition zone allowing the said fluid to pass between these two zones;

(c.) the guide zone includes continuous corrugations, the continuous corrugations of the guide zone form, with the plane ends of the heat-exchange plates, fluid circulation channels of constant cross-section and directed towards the corresponding circuits, the weak-circulation zone includes pins for maintaining separation from the plane ends of the associated heat exchange plates;

(d.) the transition zone includes longitudinally discontinuous corrugations forming passages between the guide zone and the weak-circulation zone; and (e.) the plates provided with reliefs include, at their longitudinal edges, blocks for attachment on and separation from the plane ends of the heat-exchange plates, each set formed by the ends of the heat-exchange plates, the plates provided with reliefs and the blocks is secured in leak-tight fashion to the longitudinal edges of the plates forming the transfer and exchange zone by the connection means of these plates.

Substantially all the heat transfer in the plate exchanger takes place inside the bundle which is, preferably, operated in counter-current flow. The bundle is made of thin stainless steel, corrugated sheets which are stacked and welded together. There are, preferably, no gaskets in the bundle.

The bundle is set inside the pressure vessel which is pressurized with any convenient gas, or process fluid. There is no requirement for fluid circulation inside the pressure vessel, which is, typically, used solely to withstand the operating pressure and to protect the bundle. The pressure vessel is, preferably, set horizontally with the plates vertically on edge and operates in counterflow.

Bellows compensate for the thermal differential expansion between the stainless steel bundle and the low alloy pressure vessel. The bellows are located inside the pressure vessel, between the bundle inlet/outlet pipes and the vessel nozzles.

Processes of this invention are suitable for use in purification of relatively impure aromatic carboxylic acids. Generally, the impure carboxylic acid is a crude product of catalytic, liquid-phase oxidation of a corresponding aromatic.

The current invention is particularly suitable for use in the purification of relatively impure aromatic dicarboxylic acids produced by liquid-phase oxidation of a corresponding benzene having two oxidizable alkyl or acyl ring substituents or an oxidizable alkyl and acyl ring substituent in the meta or para positions, i.e. non-adjacent, or naphthalene having two oxidizable alkyl or acyl ring substituents or an oxidizable alkyl and acyl ring substituents, but can also be crude acid product recovered from waste polyester resins comprising repeating units of the aromatic dicarboxylic acid residue and repeating units of dihydric alcohol residue.

Suitable solvents for use in the current invention include any fluid in which the material to be crystallized can be dissolved and from which the material can be crystallized. Another aspect of the solvent is that any impurities also present in the solvent along with the material to be crystallized remain soluble in the solvent at the same temperatures and pressures at which the material is crystallized. In many instances these solvents include, for example, water, acetic acid and a mixture of meta-xylene and para-xylene.

The current invention is especially useful for the recovery of terephthalic acid of a purity of 99.9 percent and higher from terephthalic acid contaminated with para-toluic acid in such amounts as preferably 200 to 5000 parts per million (ppm), desirably 200 to 10,000 ppm and suitably up to 15,000 ppm (1.5 weight percent). The process of the present invention can be used to separate substantially pure, e.g. 99.9 to 99.99 weight percent, terephthalic acid from an impure terephthalic acid containing up to about two percent para-toluic acid. The current invention can also be used to obtain terephthalic acid of 99.9 to 99.99 weight percent purity from terephthalic acid contaminated with more than about 2 weight percent, for example, up to 5 to 10 weight percent or more, para-toluic acid Depending on aromatic feed material oxidized, components of catalyst selected, levels of catalyst components selected and oxidation reaction conditions used, the reaction mixture produced in the oxidation reaction contains, in addition to the desired aromatic carboxylic acid, a number of impurities and reaction co-products. For example, terephthalic acid impurities are of several types. The material 4-carboxybenzaldehyde, an intermediate product in the oxidation of para-xylene, is found in impure terephthalic acid. Unidentified color-forming precursors and color bodies, possibly of the benzil, fluorenone or anthraquinone structure, are also usually present.

Where an aromatic acid product of higher purity is desired, processes of the present invention further include catalytically purifying the relatively impure ("crude") aromatic acid by contacting the aqueous solution of the relatively impure acid with a bed of purification catalyst at elevated temperatures and in the presence of a hydrogen-containing gas. The purification catalyst typically comprises an insoluble Group VIII noble metal on a support. Most, if not all, of the impurities in the impure acid are occluded in the crystals of crude acid. By dissolving the crude acid crystals in water, these impurities are released into the solution, and are available to be exposed to the purification catalyst.

Separation of relatively pure aromatic dicarboxylic acid from aqueous solution is, generally, carried out by crystallization at temperatures in a range upward from about 25° C. to about 200° C. or even higher temperatures. Separation of purified terephthalic acid from its mother liquor is effected while maintaining temperatures within a range downward from about 100° C. to about 25° C., preferably while maintaining temperatures within and below the range of from about 100° C. to about 75° C., more preferably while maintaining temperatures within and below the range of from about 100° C. to about 85° C.

Crystallization and separation of purified naphthalene dicarboxylic acid from the aqueous solution is, generally, effected while maintaining temperatures in a range downward from about 175° C., preferably while maintaining temperatures within and below the range of from about 150° C. to about 25° C.

Pressure conditions for the process of this invention depend upon the manner in which this process is conducted. Generally, the pressure requirements are dictated by solubility characteristics of the material to be crystallized in the solvent employed. For example, the temperatures at which the impure terephthalic acid is dissolved in water are substantially above the normal boiling point of water. Since the current invention is carried out in a manner to maintain a liquid phase of the solution, when the material to be crystallized in terephthalic acid dissolved in water, the process pressure is necessarily carried above atmospheric pressure. In the case of terephthalic acid in water, total pressures at and above the sum of the partial pressures of water vapor and hydrogen at the chosen operating temperatures are preferred.

Catalysts suitable for use in the catalytic purification are insoluble under the conditions employed and comprise at least one supported Group VIII noble metal, which group includes: palladium, rhodium, ruthenium, osmium, iridium, and platinum. The noble metal preferably is palladium or rhodium, and more preferably is palladium.

Optionally, effluent aqueous solution from the bed containing noble metal on a titanium dioxide support is passed through a subsequent particulate bed of another purification catalyst in the presence of a hydrogen-containing gas. Hydrogenation of the aqueous solution subsequent to decarbonylation further reduces organic impurities in aromatic dicarboxylic acid recovered by crystallization and separation from the aqueous solution.

Aqueous solution directly from the plate exchanger or the effluent aqueous solution from the bed containing noble metal on a titanium dioxide support is, generally, purified by reduction of impurities therein, for example, by the methods disclosed in the aforesaid U.S. Pat. Nos. 3,584,039; 3,726,915; and 4,405,809. The hydrogenation step according to the present invention for producing purified terephthalic acid, purified isophthalic acid, or purified naphthalene dicarboxylic acid is conducted at an elevated temperature and pressure in a fixed catalyst bed. The effluent aqueous solution to be purified contains, typically, from about 5 to about 50 weight percent of the aromatic dicarboxylic acid to be purified dissolved in water or a like polar solvent used in decarbonylation. Although water is the preferred solvent, other suitable polar solvents include the relatively lower molecular weight alkyl carboxylic acids containing from 2 to 6 carbon atoms, typically acetic acid, either alone or admixed with water.

When the acid which is being purified is terephthalic acid or isophthalic acid, water is the preferred solvent. When the acid being purified is a naphthalene dicarboxylic acid, a relatively higher purification temperature is employed and a solvent like acetic acid or a mixture of acetic acid and water containing from about 10 to about 90 weight percent of water is the preferred solvent because of its relatively lower vapor pressure. Suitable reactor temperatures for use in this purification step are in the range of from about 100° C. to about 350° C. Preferably, the temperatures employed in the purification step are in the range of about 225° C. to about 300° C.

After hydrogenation, the treated acid solution is separated from the solid catalyst particles. The purified acid is crystallized from the separated solution by cooling it, to a temperature for example, about 150° C. or below, that is sufficiently low for crystallization of the purified acid to occur but sufficiently high that the impurities and their reduction products remain dissolved in the resultant mother liquor. Thereafter the mother liquor containing the dissolved impurities and the reduction products is separated from the crystallized purified acid, whereby crystals are recovered.

Terephthalic acid concentration in the solution to be purified by hydrogenation can vary over a relatively wide range. Concentration can be as low as about 5 percent by weight or as high as about 50 percent by weight, based on the weight of the solution. Preferably, the solution concentration of terephthalic acid is in a range of from about 20 to about 40 percent by weight.

Processes of this invention need not be carried out by using only one plate heat exchanger for they can be carried out with a plurality of plate heat exchangers as a matter of choice or as the solubility vs. temperature curve of the particular material to be recovered indicates when taken into account as herein described.

The crystallization technique of this invention is illustrated by the following Examples which are presented in order to better communicate the invention. The Examples are not intended to limit the scope of the invention in any way.

EXAMPLE 1

The crystallization technique of this invention is carried out starting with an aqueous solution of terephthalic acid at 270° C. (about 520° F.) and 985 psig (6900 kPa) having 30 pounds dissolved terephthalic acid per 100 pounds of water and 600 ppm para-toluic acid based on the solution (2600 ppm based on terephthalic acid). The 270° C. aqueous solution of terephthalic acid is fed continuously through horizontal channels of a plate heat exchanger and counter-currently to coolant flowing through adjacent channels. The aqueous solution is thereby cooled to 105° C. (about 220° F.) to effect separation of relatively pure terephthalic acid from resulting mother liquor by crystallization. This slurry is continuously fed to centrifuges to separate the purified terephthalic acid crystals from the mother liquor. The purified terephthalic acid centrifuge cake is washed with water and then dried.

In the foregoing manner dried terephthalic acid may be recovered in yields of 99.5 percent based in the terephthalic acid originally present in the 270° C. feed solution. The para-toluic acid content of the dried terephthalic acid is in the 90 ppm to 120 ppm range. Thus a "separation factor" in the range of 22 to 29 is achieved. The term "separation factor" is the ratio of original impurity, for example para-toluic acid, present to than in the recovered and dried product.

EXAMPLE 2

Using the plate heat exchanger system of Example 1 crystallization in accordance with this invention is carried out starting with an aqueous solution of isophthalic acid at 220° C. (about 428° F.) and 500 psig (3400 kPa) having 40 pounds dissolved isophthalic acid per 100 pounds of water and 300 ppm meta-toluic acid based on the solution (1000 ppm based on isophthalic acid). The 220° C. aqueous solution of isophthalic acid is fed continuously through horizontal channels of a plate heat exchanger and counter-currently to coolant flowing through adjacent channels. The aqueous medium is thereby cooled to 95° C. (about 203° F.) to effect separation of relatively pure isophthalic acid from resulting mother liquor by crystallization. This slurry is continuously fed to centrifuges to separate purified isophthalic acid crystals from the mother liquor. The purified isophthalic acid centrifuge cake is washed with water and then dried.

In the foregoing manner dried isophthalic acid may be recovered in yields of 98 percent based in the isophthalic acid originally present in the 220° C. feed solution. The meta-toluic acid content of the dried isophthalic acid is in the range of 20 to 50 ppm. Thus a "separation factor" in the range of 6 to 15 is achieved.

EXAMPLE 3

Using the plate heat exchanger system of Example 1 crystallization in accordance with this invention is carried out with a crude 2,6-naphthalene dicarboxylic acid having an assay as follows: 98 percent 2,6-naphthalene dicarboxylic acid, 1 percent trimellitic acid, 0.3 percent 6-formal-2-naphthoic acid, plus various metallic impurities and unidentified color bodies. An aqueous solution of the crude 2,6-naphthalene dicarboxylic acid is prepared at 315° C. (about 600° F.) which has 20 pounds dissolved 2,6-naphthalene dicarboxylic acid per 100 pounds of water. The 315° C. aqueous solution of 2,6-naphthalene dicarboxylic acid is fed continuously through horizontal channels of a plate heat exchanger and counter-currently to coolant flowing through adjacent channels. The aqueous medium is thereby cooled to 215° C. (about 420° F.) to effect separation of relatively pure 2,6-naphthalene dicarboxylic acid from resulting mother liquor by crystallization. This slurry is fed to centrifuges continuously to separate 2,6-naphthalene dicarboxylic acid crystals from the mother liquor. The 2,6-naphthalene dicarboxylic acid centrifuge cake is washed with water and then dried.

In the foregoing manner dried 2,6-naphthalene dicarboxylic acid may be recovered in yields of 90 percent based in the 2,6-naphthalene dicarboxylic acid originally present in the 315° C. feed solution. The trimellitic acid content of the dried 2,6-naphthalene dicarboxylic acid is in the 100 to 150 ppm range.

EXAMPLE 4

Using the plate heat exchanger system of Example 1 crystallization in accordance with this invention is carried out starting with an aqueous solution of 2,6-naphthalene dicarboxylic acid at 315° C. (about 600° F.) having 20 pounds dissolved 2,6-naphthalene dicarboxylic acid per 100 pounds of water and 0.3 percent 6-methyl-2-naphthoic acid based on 2,6-naphthalene dicarboxylic acid. The 315° C. aqueous solution of 2,6-naphthalene dicarboxylic acid is continuously fed through horizontal channels of a plate heat exchanger and counter-currently to coolant flowing through adjacent channels. The aqueous medium is thereby cooled to 215° C. (about 420° F.) to effect separation of relatively pure 2,6-naphthalene dicarboxylic acid from resulting mother liquor by crystallization. This slurry is fed to centrifuges continuously to separate 2,6-naphthalene dicarboxylic acid crystals from the mother liquor. The 2,6-naphthalene dicarboxylic acid centrifuge cake is washed with water and then dried.

In the foregoing manner dried 2,6-naphthalene dicarboxylic acid may be recovered in yields of 90 percent based in the isophthalic acid originally present in the 315° C. feed solution. The 6-methyl-2-naphthoic acid content of the dried 2,6-naphthalene dicarboxylic acid is in the 100 to 500 ppm range. The purity of dried 2,6-naphthalene dicarboxylic acid is in the range of 99.5 to 99.9 percent.

What is claimed is:

1. A process for crystallizing an aromatic carboxylic acid comprising:
   (a) providing a plate heat exchanger comprising a plurality of substantially parallel plates, wherein the plurality of substantially parallel plates are disposed to form a first circuit and a second circuit;
   (b) passing a solution comprising a crystallizable aromatic carboxylic acid through the first circuit in a heat exchange relationship with a heat exchange fluid flowing in the second circuit;
   whereby the aromatic carboxylic acid is crystallized, and wherein crystallized aromatic carboxylic acid is prevented from plugging the first circuit by flow characteristics of the solution.

2. A process for crystallizing a crystallizable aromatic organic material selected from the group consisting of para-xylene, meta-xylene and dimethylnaphthalene comprising:
   (a) providing a plate heat exchanger comprising a plurality of substantially parallel plates, wherein the plurality of substantially parallel plates are disposed to form a first circuit and a second circuit;
   (b) passing a solution comprising a crystallizable aromatic organic material selected from the group consisting of para-xylene, meta-xylene and dimethylnaphthalene through the first circuit in a heat exchange relationship with a heat exchange fluid flowing in the second circuit;
   whereby the crystallizable aromatic organic material is crystallized, and wherein crystallized aromatic organic material is prevented from plugging the first circuit by flow characteristics of the solution.

3. The process according to claim 1 wherein the aromatic carboxylic acid is selected from the group consisting of phthalic acid, terephthalic acid, isophthalic acid, trimellitic acid, naphthalenedicarboxylic acid, tertiery-butyl isophthalic acid, biphenyldicarboxylic acid, pyromellitic acid, and oxybisbenzoic acid.

4. The process according to claim 1 wherein the solution further comprises alkyl carboxylic acids containing from 2 to 6 carbon atoms.

5. The process according to claim 4 wherein the solution further comprises acetic acid.

6. The process according to claim 4 wherein the solution further comprises water.

7. A process for purifying a crude aromatic carboxylic acid comprising:
   (a) providing a plate heat exchange comprising a plurality of substantially parallel plate, wherein the plurality of substantially parallel plates are disposed to form a first circuit and a second circuit;
   (b) preparing a first solution of crude aromatic carboxylic acid by heating a first slurry comprising solid particulates of crude aromatic carboxylic acid and a solvent in the first circuit until the solid particulates are substantially dissolved therein;
   (c) passing the first solution through a catalytic purification reactor having an amount of purification catalyst disposed therein, wherein at least a portion the amount of purification catalyst is contacted by at least a portion of the first solution, whereby a second solution is formed, the second solution comprising purified aromatic carboxylic acid and a fluid medium; and
   (d) cooling the second solution in the second circuit until the purified aromatic carboxylic acid is crystallized whereby a second slurry is formed, the second slurry comprising crystals of purified aromatic carboxylic acid and the fluid medium.

8. The process according to claim 7 further comprising:
   (d) physically separating the crystals of purified aromatic carboxylic acid from the liquid medium.

9. The process according to claim 7 wherein the aromatic carboxylic acid is selected from the group consisting of phthalic acid, isophthalic acid, terephthalic acid, tertiery-butyl isophthalic acid, biphenyldicarboxylic acid, pyromellitic acid, trimellitic acid, oxybisbenzoic acid and naphthalene dicarboxylic acid.

10. The process according to claim 7 wherein the first slurry and the second slurry flow countercurrently to each other in the plate heat exchanger.

11. The process according to claim 2, claim 1, or claim 7 wherein the plate heat exchanger is disposed in a pressurized vessel.

12. The process according to claim 11 wherein the pressurized vessel is maintained at a pressure of at least about 400 psig.

13. The process according to claim 11 wherein the pressurized vessel is maintained at a pressure at least about 500 psig.

* * * * *